United States Patent [19]
Maracas

[11] Patent Number: 6,048,691
[45] Date of Patent: Apr. 11, 2000

[54] METHOD AND SYSTEM FOR PERFORMING A BINDING ASSAY

[75] Inventor: George N. Maracas, Phoenix, Ariz.

[73] Assignee: Motorola, Inc., Schaumburg, Ill.

[21] Appl. No.: 08/859,513

[22] Filed: May 20, 1997

Related U.S. Application Data

[63] Continuation-in-part of application No. 08/648,635, May 13, 1996, Pat. No. 5,731,152.

[51] Int. Cl.$^7$ ........................................... C12Q 1/68
[52] U.S. Cl. ........................... 435/6; 636/23.1; 636/24.3; 935/76; 935/77; 935/78
[58] Field of Search .......................... 435/6, 7.1; 935/76, 935/77, 78; 536/23.1, 24.3

[56] References Cited

U.S. PATENT DOCUMENTS

| | | | |
|---|---|---|---|
| 5,068,176 | 11/1991 | Vijg et al. | 435/6 |
| 5,110,833 | 5/1992 | Mosbach . | |
| 5,310,648 | 5/1994 | Arnold et al. . | |
| 5,324,633 | 6/1994 | Fodor et al. | 435/6 |
| 5,364,793 | 11/1994 | Cameron, Sr. et al. | 436/86 |
| 5,372,719 | 12/1994 | Afeyan et al. . | |
| 5,424,186 | 6/1995 | Fodor et al. | 435/6 |
| 5,449,754 | 9/1995 | Nishioka | 530/334 |
| 5,453,199 | 9/1995 | Afeyan et al. . | |
| 5,461,175 | 10/1995 | Fischer et al. . | |
| 5,472,672 | 12/1995 | Brennan | 422/131 |
| 5,489,678 | 2/1996 | Fodor et al. | 536/22.1 |
| 5,492,806 | 2/1996 | Drmanac et al. | 435/5 |
| 5,503,980 | 4/1996 | Cantor | 435/6 |
| 5,527,681 | 6/1996 | Holmes | 435/6 |
| 5,529,756 | 6/1996 | Brennan | 422/131 |
| 5,541,342 | 7/1996 | Korhonen et al. . | |
| 5,545,531 | 8/1996 | Rava et al. | 435/6 |
| 5,547,839 | 8/1996 | Dower et al. | 435/6 |
| 5,571,639 | 11/1996 | Hubbell et al. | 430/5 |
| 5,587,273 | 12/1996 | Yan et al. . | |
| 5,599,695 | 2/1997 | Pease et al. | 435/91.1 |
| 5,604,097 | 2/1997 | Brenner | 435/6 |
| 5,604,100 | 2/1997 | Perlin | 435/6 |
| 5,632,957 | 5/1997 | Heller et al. | 422/68.1 |
| 5,637,458 | 6/1997 | Frankel et al. | 435/6 |
| 5,731,152 | 3/1998 | Maracas et al. | 435/6 |

OTHER PUBLICATIONS

The New England BioLabs Catalog, pp. 188–189 (1993/94).
Allikmets et al., Genomics 19:303–309 (1994).
Sommer and Tautz, "Minimal Homology Requirements for PCR Primers", Nucleic Acids Research, vol. 17, No. 16, p. 6749, 1989.
Mendez et al., Genomics 10:661–665 (1991).
Bentley et al., Genomics 12:534–541 (1992).
Davis et al., Basic Methods in Molecular Biology, pp. 44–78, 130–146, 306–314 (1986).
Kainz et al., Analytical Biochemistry 178:260–262 (1989).

*Primary Examiner*—W. Gary Jones
*Assistant Examiner*—Ethan Whisenaut
*Attorney, Agent, or Firm*—James E. Gauger

[57] ABSTRACT

A method of performing a binding assay which comprises the steps of separating a plurality of sample fragments into a plurality of subsamples and applying each of the plurality of subsamples to a respective one of a plurality of binding assays. A system which performs the aforementioned steps is also disclosed.

22 Claims, 4 Drawing Sheets

METHOD AND SYSTEM FOR PERFORMING A BINDING ASSAY

RELATED APPLICATIONS

The present application is a continuation in part of "Methods and Systems for Biological Reagent Placement", having Ser. No. 08/648,635, filed May 13, 1996 now U.S. Pat. No. 5,731,152.

The subject matter of the above-listed application is hereby incorporated by reference into the disclosure of the present application.

TECHNICAL FIELD

The present invention relates to molecular detection devices and methods and systems for performing a binding assay therewith.

BACKGROUND OF THE INVENTION

Recent efforts have been directed in developing chips for molecular detection. Of particular interest are DNA chips for sequencing and diagnostic applications. A DNA chip includes an array of chemically-sensitive binding sites having single-stranded DNA probes or like synthetic probes for recognizing respective DNA sequences. A sample of single-stranded DNA is applied to all of the binding sites of the DNA chip. The DNA sample attaches to DNA probes at one or more of the binding sites. The sites at which binding occurs are detected, and one or more molecular structures within the sample are subsequently deduced.

In sequencing applications, a sequence of nucleotide bases within the DNA sample can be determined by detecting which probes have the DNA sample bound thereto. In diagnostic applications, a genomic sample from an individual is screened with respect to a predetermined set of probes to determine if the individual has a disease or a genetic disposition to a disease.

FIG. 1 illustrates a potential hybridization error which can occur with a DNA chip. In this example, a sample DNA molecule 10 falsely hybridizes to a DNA probe 12. The sample DNA molecule 10 includes a first base sequence 14 and a second base sequence 16. The first base sequence 14 is separated from the second base sequence 16 by an intermediate sequence 18. The DNA probe 12 is complementary to both the first base sequence 14 and the second base sequence 16, but is not complementary to the intermediate sequence 18. Such a hybridization error can lead to errors in determining a sequence associated with the sample, or errors in performing a diagnostic using the sample.

BRIEF DESCRIPTION OF THE DRAWINGS

The invention is pointed out with particularity in the appended claims. However, other aspects of the invention are described with reference to the following detailed description and the accompanying drawings in which:

DETAILED DESCRIPTION OF A PREFERRED EMBODIMENT

Embodiments of the present invention reduce a likelihood of false hybridization by not applying an entire sample to all binding sites. In particular, a sample is preprocessed using a restriction enzyme cutting technique to form sample fragments. The sample fragments are separated by size into subsamples. Each subsample is applied to a respective set of binding sites having molecular receptors specifically designed for fragment sizes therein. Embodiments of the present invention are amenable for use in performing multiple assays on a single chip.

Figure 1:
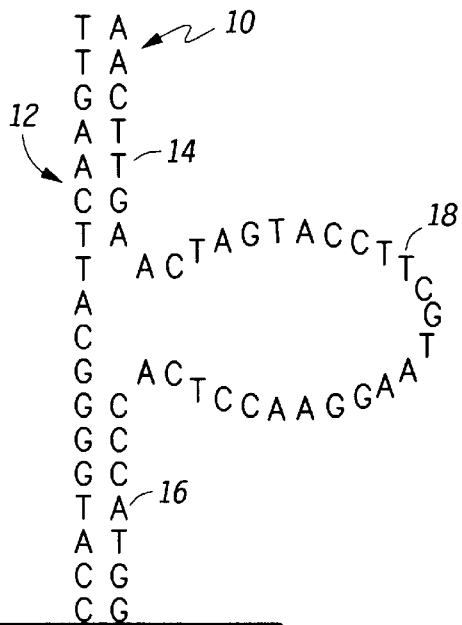
FIG. 1 illustrates a potential hybridization error which can occur with a DNA chip.
Figure 2:
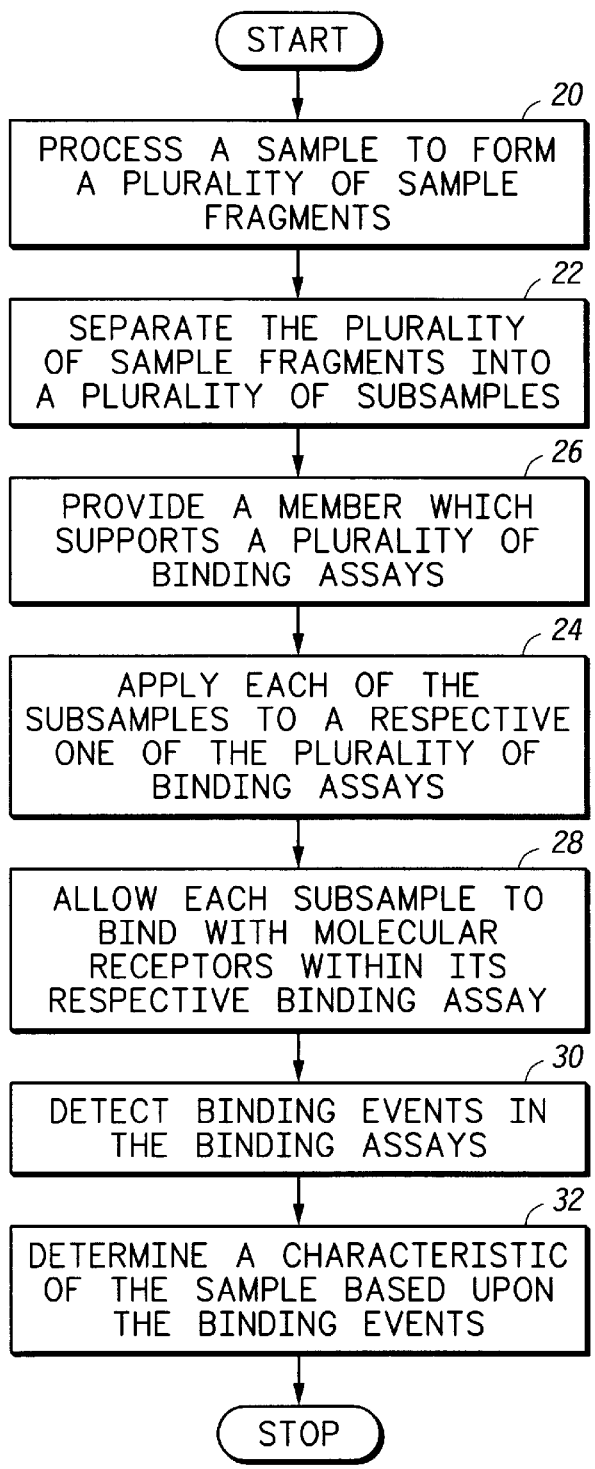
FIG. 2 is a flow chart of an embodiment of a method of performing a binding assay in accordance with the present invention.

FIG. 2 is a flow chart of an embodiment of a method of performing a binding assay in accordance with the present invention. The binding assay can be performed for a variety of applications, including but not limited to, sequencing applications, diagnostic applications, forensic applications, and human-identity applications.

As indicated by block 20, the method includes a step of processing a sample to form a plurality of sample fragments. Examples of the sample include but are not limited to a ligand sample, a nucleic acid sample, a genomic sample from an organism or a plant, and an environmental sample. Of particular interest is where the sample includes a sequence of at least one nucleotide base. In this case, the sample can include at least one polynucleotide molecule such as DNA or RNA. In addition to any necessary sample preparation steps, the step of processing preferably includes a step of cutting the at least one polynucleotide molecule into the smaller sample fragments using at least one restriction endonuclease. Various known techniques for cutting molecules using restriction enzymes can be used in this step.

As indicated by block 22, the method includes a step of separating the plurality of sample fragments into a plurality of subsamples. This step preferably includes either mass-separating or length-separating the sample fragments into the subsamples. Each subsample includes sample fragments having a length or a mass within a corresponding range. By performing the step of separating, each subsample contains like-sized sample fragments, e.g. having approximately the same mass or length.

Preferably, the ranges are nonoverlapping. For example, a first subsample can contain sample fragments having a length of between 11 and 20 bases, a second subsample can contain sample fragments having a length of between 21 and 30 bases, and a third subsample can contain sample fragments having a length of between 31 and 40 bases.

Various known methods of separating molecules can be used. A first preferred method includes electrophoresing the sample fragments to isolate the subsamples. A second preferred method includes centrifuging the sample fragments to isolate the subsamples. A third preferred method utilizes electroosmosis to isolate the subsamples.

As indicated by block 24, the method includes a step of applying each of the plurality of subsamples to a respective one of a plurality of binding assays. Each of the binding assays includes at least one molecular receptor, and typically a plurality of molecular receptors. Each molecular receptor is for binding or hybridizing with a subsample molecule having a predetermined or preselected structure.

Each molecular receptor can include a biological molecule or synthetic molecules having a specific affinity to its corresponding molecule. For example, each molecular receptor can include a chain of nucleotide bases to hybridize with a molecule having a complementary chain of nucleotide bases. In this case, each molecular receptor can include a DNA probe for detecting a corresponding, complementary DNA base sequence in a subsample, or an RNA probe for detecting a corresponding, complementary RNA base sequence in a subsample.

Alternatively, each molecular receptor can include a member, such as a film, having an affinity to a corresponding molecule in a subsample. For example, each film can be molecular imprinted in accordance with U.S. Pat. No. 5,587,273 to Yan et al., which is hereby incorporated by reference into the present disclosure. In this case, each film is molecularly imprinted using a corresponding imprinting molecule. Other examples of molecular receptors are given in U.S. Pat. Nos. 5,110,833, 5,310,648, 5,372,719, 5,453,199, 5,461,175, and 5,541,342 which are hereby incorporated by reference into the present disclosure.

As another alternative, each molecular receptor can include an imprinted matrix in accordance with U.S. Pat. No. 5,310,648 to Arnold et al., which is hereby incorporated by reference into the present disclosure.

Preferably and advantageously, each binding assay is specifically designed for a known range of fragment sizes in its subsample. In particular, the molecular receptors in a binding assay has a length of bases approximately equal to the length of each sample fragment in its corresponding subsample. For example, the aforementioned first subsample containing sample fragments between 11 and 20 bases in length can be applied to a first binding assay comprised of molecular receptors having a length of 20 bases. Similarly, the aforementioned second subsample containing sample fragments between 21 and 30 bases in length can be applied to a second binding assay comprised of molecular receptors having a length of 30 bases. Further, the aforementioned third subsample containing sample fragments between 31 and 40 bases in length can be applied to a third binding assay comprised of molecular receptors having a length of 40 bases.

Preferably, prior to applying the subsamples, a step of providing a member which supports the binding assays is performed as indicated by block 26. The member can be formed of various materials including semiconductive materials, conductive materials, and dielectric materials. Examples of preferred materials include, but are not limited to silicon, glass, metals, polymers, and plastics.

Although the binding assays can be supported by the member to have any arrangement in general, it is preferred that the binding assays be arranged as a one-dimensional array or a two-dimensional array. Similarly, although the binding sites within each binding assay can have any arrangement in general, it is preferred that each binding assay comprises a two-dimensional array of binding sites.

Preferably, the member includes a substrate having a surface which supports the molecular receptors of the binding assays. The molecular receptors can be bound to the surface using a primer, a gel, or an adhesive, or can be integrated with the surface using a molecular imprinting approach. Alternatively, like ones of the molecular receptors can be supported by a corresponding member placed on the surface. For example, molecular receptors can be contained in a prepatterned gel member placed on the surface.

By supporting all of the binding assays with a single member, the subsamples can be applied to the binding assays in accordance with the pending patent application entitled "Methods and Systems for Biological Reagent Placement", Ser. No. 08/648,635 now U.S. Pat. No. 5,731,152 incorporated by reference into the present disclosure. In this case, the step of applying can include steps of providing an applicator or a stamp member having a plurality of transfer elements, loading each of the plurality of subsamples to a respective one of the plurality of transfer elements, and contacting the applicator to the substrate. Each transfer element corresponds to a respective one of the binding assays.

Thereafter, each subsample is allowed to bind or hybridize with molecular receptors within its respective binding assay, as indicated by block 28. Preferably, the applicator is maintained in contact with the member or the substrate at least until binding in at least one binding assay has completed. More preferably, the applicator is maintained in contact with the substrate until binding in each of the binding assays has completed.

Additionally, each subsample can be amplified while the applicator is maintained in contact with the member or the substrate. For example, a PCR (polymerase chain reaction) amplification technique can be performed while the applicator contacts the member or the substrate as taught in the reference "Methods and Systems for Biological Reagent Placement" incorporated by reference into the present disclosure.

As indicated by block 30, the method includes a step of detecting binding events in the binding assays. The binding events can be detected using various known techniques including but not limited to optical detection techniques, electronic detection techniques, radioactive detection techniques, and chemical detection techniques. The step of detecting the binding events can be performed while the applicator is maintained in contact with the substrate, or after the applicator is removed from the substrate.

As indicated by block 32, the method includes a step of determining a characteristic of the sample and/or of the sample fragments based upon the binding events. Examples of the step of determining a characteristic include but are not limited to determining a base sequence associated with the sample (e.g. for sequencing by hybridization), or determining whether a predetermined base sequence is present within the sample (e.g. for diagnostic, forensic, or identity procedures).

Figure 3:
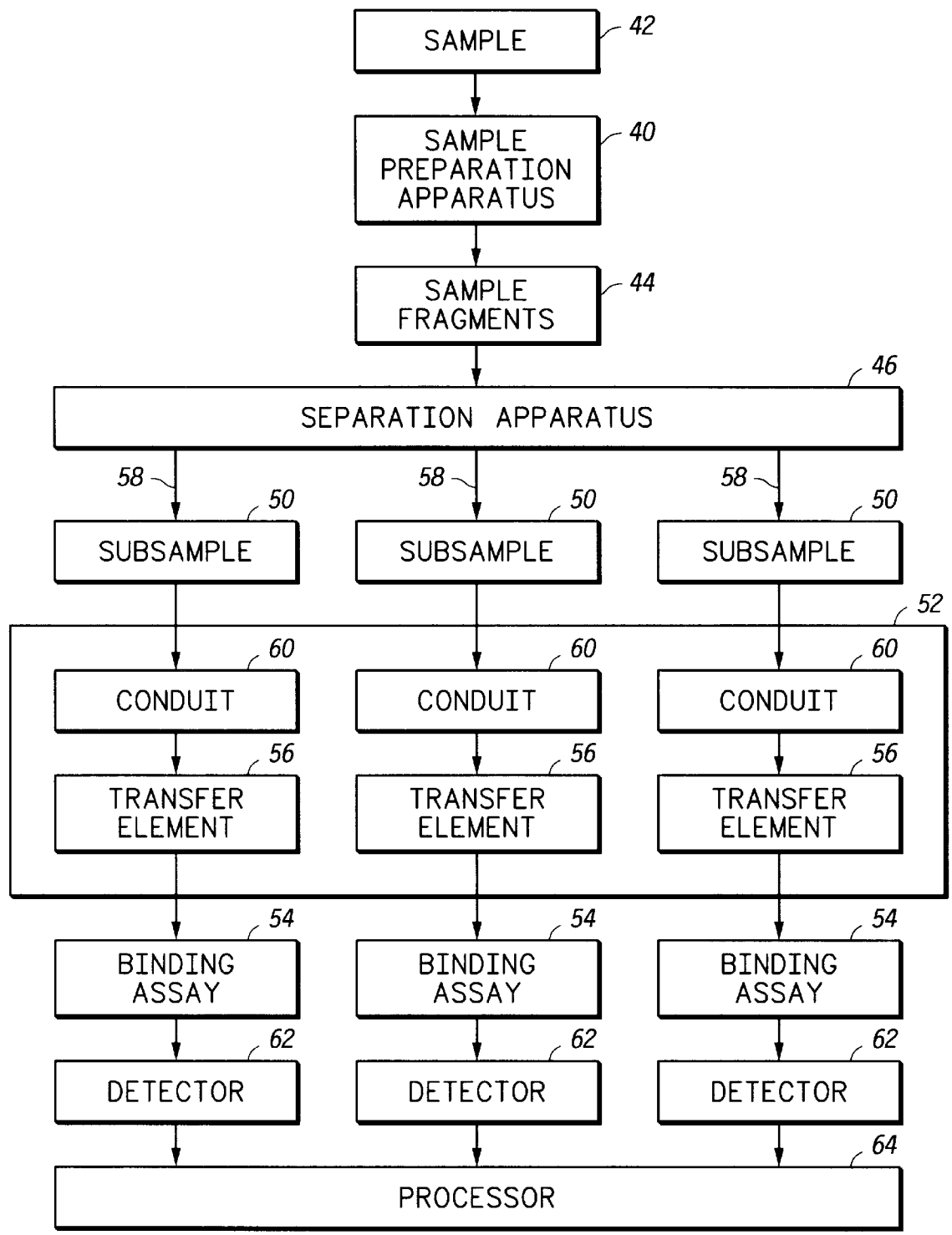
FIG. 3 is a block diagram of an embodiment of a system for performing a binding assay.

FIG. 3 is a block diagram of an embodiment of a system for performing a binding assay. The system can be used to perform the steps described with reference to FIG. 2.

The system comprises a sample preparation apparatus 40 which processes a sample 42 to form a plurality of sample fragments 44. Preferably, the sample preparation apparatus 40 cuts molecules in the sample 42 using a restriction endonuclease to form the sample fragments 44. The sample preparation apparatus 40 can also perform sample preparation steps as are known in the art.

The system further comprises a separation apparatus 46 to separate the plurality of sample fragments into a plurality of subsamples 50. A detailed description of an embodiment of the separation apparatus 46 is subsequently described with reference to FIG. 10. Generally, the separation apparatus 46 can include a mass-separation apparatus or a length-separation apparatus, such as an electrophoresis apparatus or a centrifuge.

The system includes an applicator 52 to apply each of the subsamples 50 to a respective one of a plurality of binding assays 54. Each of the binding assays 54 generally includes at least one molecular receptor as described with reference to FIG. 2. Preferably, each of the binding assays 54 includes an oligonucleotide subarray such as a combinatorial array. The length of the oligonucleotides in each subarray is approximately equal to the length of molecules in its respective subsample.

The applicator 52 includes a plurality of transfer elements 56 to transfer the subsamples 50 to the binding assays 54. The transfer elements 56 can be formed in accordance with any of the embodiments described in the reference entitled "Method and System for Biological Reagent Placement" incorporated by reference into the present disclosure.

Preferably, the separation apparatus 46 includes a plurality of outlets 58, each of the outlets 58 corresponding to a respective one of the subsamples 50. Each of the outlets 58 communicates its respective subsample to a respective one of the transfer elements 56. It is further preferred that the applicator 52 includes a plurality of conduits 60 to couple the outlets 58 to the transfer elements 56.

Preferably, the binding assays 54 are all supported by a member described with reference to FIG. 2. In this case, the applicator 52 can apply each of the subsamples 50 to its respective one of the binding assays 54 by contacting the member.

The system includes one or more detectors 62 to detect binding events in the binding assays 54. The detectors 62 detect which molecular receptors hybridize or bind with subsample molecules. The detectors 62 can include optical detectors, electronic detectors, radioactivity detectors, or chemical detectors, for example, as are known in the art.

The system includes a processor 64 responsive to the detectors 62 to determine a characteristic of the sample 42 and/or of the sample fragments 44. The processor 64 can include a computer or other like processing apparatus.

FIGS. 4 to 9 illustrate an example of performing a binding assay for a DNA sample. For the purpose of illustration, the binding assay is performed for a DNA sample. It is noted, however, that the teachings in the example can apply for other samples such as a ligand sample, a nucleic acid sample, a polymer sample, a polynucleotide sample, or an RNA sample.

Figure 4:
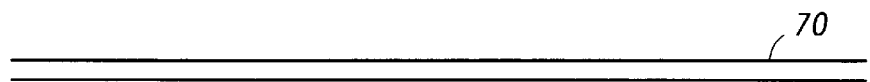
FIG. 4 is a schematic illustration of a DNA molecule in a DNA sample to be analyzed.

FIG. 4 is a schematic illustration of a DNA molecule 70 in a DNA sample to be analyzed. Although the DNA molecule is illustrated as being double-stranded, a single-stranded DNA molecule can be substituted therefor.

Figure 5:
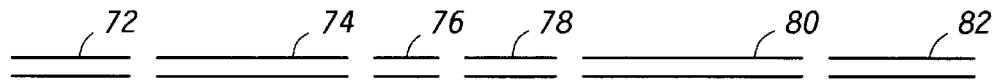
FIG. 5 is a schematic illustration of a plurality of sample fragments produced by cutting the DNA molecule of FIG. 4 with a restriction endonuclease.

FIG. 5 is a schematic illustration of a plurality of sample fragments produced by cutting the DNA molecule 70 of FIG. 4 with a restriction endonuclease. For purposes of illustration and example, the sample fragments includes a first fragment 72, a second fragment 74, a third fragment 76, a fourth fragment 78, a fifth fragment 80, and a sixth fragment 82. The sample fragments can be ordered from smallest in length to largest in length as follows: the third fragment 76, the fourth fragment 78, first fragment 72, the sixth fragment 82, the second fragment 74, and the fifth fragment 80.

Figure 6:
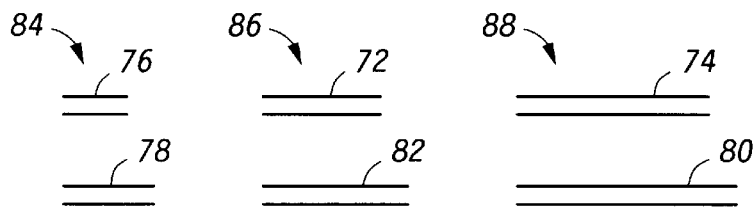
FIG. 6 is a schematic illustration of a plurality of subsamples which result after separating the sample fragments of FIG. 5.

FIG. 6 is a schematic illustration of a plurality of subsamples which result after separating the sample fragments of FIG. 5. The subsamples include a first subsample 84 of short fragments, a second subsample 86 of intermediate length fragments, and a third subsample 88 of long fragments. In this example, the first subsample 84 includes the third fragment 76 and the fourth fragment 78. The second subsample 86 includes the first fragment 72 and the sixth fragment 82. The third subsample 88 includes the second fragment 74 and the fifth fragment 80. It is noted that the sample fragments can be isolated into any number of subsamples in general.

Figure 7:
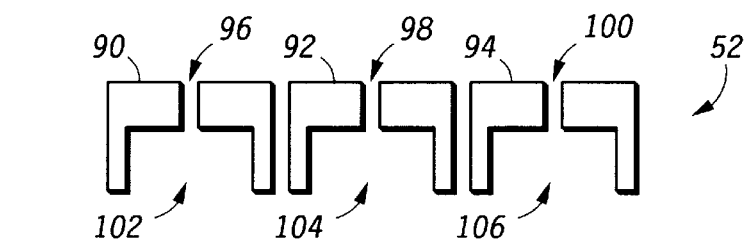
FIG. 7 is an illustration of an embodiment of an applicator to apply the subsamples of FIG. 6 to a plurality of binding assays.

FIG. 7 is an illustration of an embodiment of the applicator 52 to apply the subsamples of FIG. 6 to a plurality of binding arrays. The applicator 52 includes a first transfer element 90, a second transfer element 92, and a third transfer element 94. The first subsample 84 is loaded into the first transfer element 90 by a conduit 96. The second subsample 86 is loaded into the second transfer element 92 by a conduit 98. The third subsample 88 is loaded into the third transfer element 94 by a conduit 100.

The first transfer element 90 includes a reservoir or cavity 102 which receives the first subsample 84 from the conduit 96. The second transfer element 92 includes a reservoir or cavity 104 which receives the second subsample 86 from the conduit 98. The third transfer element 94 includes a reservoir or cavity 106 which receives the third subsample 88 from the conduit 100. Adjacent pairs of the cavities 102, 104, and 106 are physically separated and have a barrier or wall therebetween to avoid crosstalk of subsamples between transfer elements.

Figure 8:
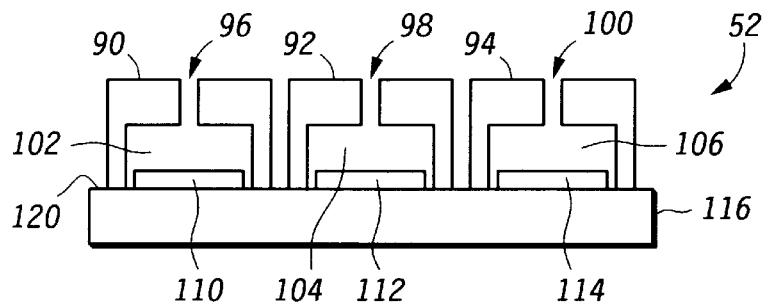
FIG. 8 is a side sectional view of the applicator of FIG. 7 applying the subsamples to a plurality of binding assays.

FIG. 8 is a side sectional view of the applicator 52 of FIG. 7 applying the subsamples to a plurality of binding assays. The first transfer element 90 applies the first subsample 84 to a first binding assay 110. The second transfer element 92 applies the second subsample 86 to a second binding assay 112. The third transfer element 94 applies the third subsample 88 to a third binding assay 114.

The binding assays 110, 112, and 114 are supported by a substrate 116. The applicator 52 applies the subsamples 84, 86, and 88 by contacting a surface 120 of the substrate 116. When the applicator 52 contacts the surface 120, the cavity 102 encloses the first binding assay 110, the cavity 104 encloses the second binding assay 112, and the cavity 106 encloses the third binding assay 114. As a result, binding or hybridization reactions are contained within each of the cavities 102, 104, and 106. Further, chemical crosstalk or cross contamination between binding assays is avoided.

Figure 9:
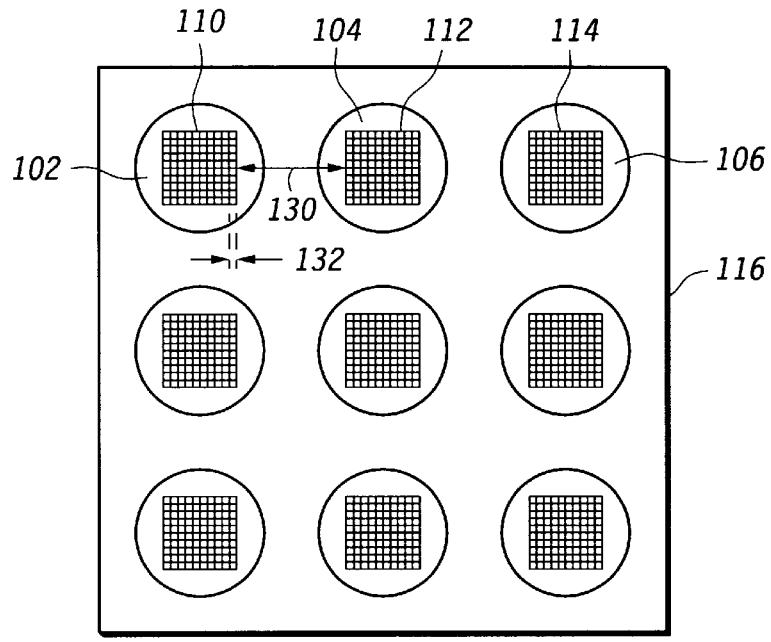
FIG. 9 is a top sectional view of the applicator applying the subsamples to the binding assays.

FIG. 9 is a top sectional view of the applicator 52 applying the subsamples to the binding assays. In this example, each binding assay comprises a two-dimensional array of binding sites. Each binding site has one or more molecular receptors specific to a predetermined DNA sequence. The length of the molecular receptors in each array is approximately equal to the length of molecules in its respective subsample.

A distance 130 between adjacent assays is greater than a distance 132 between adjacent binding sites in the assays. This spacing assists in avoiding cross contamination of subsamples between binding assays, while densely supporting binding sites within each assay.

Although illustrated to have an equal number of binding sites in each binding assay, it is noted that the binding assays can generally have different numbers of binding sites. For example, one binding assay can include a 256-by-256 array of all possible oligonucleotides having eight bases, while another binding assay includes a 16-by-16 array of all possible oligonucleotides having four bases.

It is further noted that many binding assays can be supported by the substrate 116, in general.

Figure 10:
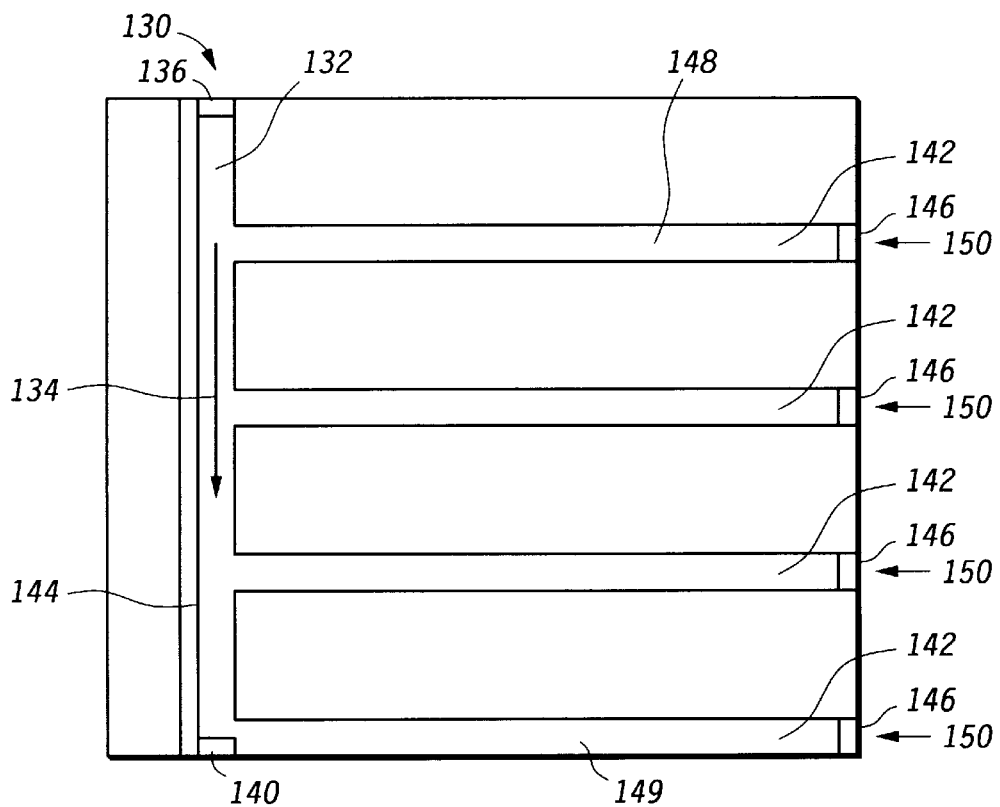
FIG. 10 is a view of an embodiment of a separation apparatus to separate the sample fragments into the subsamples.

FIG. 10 is a view of an embodiment of a separation apparatus to separate the sample fragments into the subsamples. This embodiment of the separation apparatus separates the sample fragments using a known effect of either electrophoresis or electroosmosis.

The separation apparatus includes an inlet 130 which receives sample fragments. The inlet 130 communicates the sample fragments to a channel 132. The sample fragments migrate through the channel 132 in response to an electric field along an axis 134. The electric field is generated by applying a voltage between a first electrode 136 at a first end of the channel 132 and a second electrode 140 at a second end of the channel 132.

Distributed along the length of the channel 132 are a plurality of channels 142. The channels 142 are oriented transverse to the channel 132, and preferably are oriented perpendicular to the channel 132. The channels 142 are coupled to the channel 132 to receive sample fragments in response to electric fields perpendicular to the axis 134. The electric fields are generated by applying a voltage across an electrode 144 and electrodes 146.

To separate the sample fragments into subsamples, a voltage is applied across the first electrode 136 and the second electrode 140 to induce migration of the sample fragments through the channel 132. Lower-mass fragments migrate faster through the channel 132 than do higher-mass fragments.

Thereafter, voltages are applied between the electrode 144 and the electrodes 146 to generate electric fields in the channels 142. The voltages can be applied after a predetermined time duration, or once the lower-mass fragments migrate a predetermined distance along the channel 142. At this time, the voltage can be removed between the first electrode 136 and the second electrode 140 to remove the electric field along the axis 134.

The electric fields induce migration of the sample fragments from the channel 132 to the channels 142. Each sample fragment migrates to one of the channels 142 proximate thereto at the time the electric fields are generated. As a result, the channels 142 provide an ordering of sample fragment sizes, from channel 148 containing a subsample having the largest sample fragments to channel 149 containing a subsample having the smallest sample fragments.

The subsamples migrate through the channels 142 to a plurality of outlets 150. Each of the outlets 150 is coupled to a respective one of the conduits of the applicator 52 to communicate the subsamples to the transfer elements. Each of the outlets 150 can be coupled by a tube or a like conduit to its respective conduit in the applicator 52.

Thus, there has been described herein several embodiments including preferred embodiments of a method and system for performing a binding assay.

Because the various embodiments of the present invention apply sample fragments to a limited number of binding sites, they provide a significant improvement in reducing a likelihood of a hybridization error.

Additionally, the various embodiments of the present invention as herein-described enclose each binding assay during hybridization to reduce a likelihood of cross contamination of subsamples.

It is noted that the teachings herein can be extended to non-DNA samples, and more generally, to any application where different chemical reactions are to be performed at different locations. As such, the teachings herein can be applied to assays other than binding assays.

It will be apparent to those skilled in the art that the disclosed invention may be modified in numerous ways and may assume many embodiments other than the preferred form specifically set out and described above.

Accordingly, it is intended by the appended claims to cover all modifications of the invention which fall within the true spirit and scope of the invention.

What is claimed is:

1. A method comprising the steps of:

separating a plurality of sample fragments into a plurality of subsamples including a first subsample and a second subsample;

applying the first subsample to a first binding assay for detecting any of $4^m$ different base sequences having a length of m bases; and applying the second subsample to a second binding assay for detecting any of $4^n$ different base sequences having a length of n bases.

2. The method of claim 1 wherein the step of separating the plurality of sample fragments includes electrophoresing the plurality of sample fragments.

3. The method of claim 1 wherein the step of separating the plurality of sample fragments includes centrifuging the plurality of sample fragments.

4. The method of claim 1 wherein the step of separating the plurality of sample fragments includes separating the plurality of sample fragments based upon a corresponding mass of each of the plurality of sample fragments.

5. The method of claim 1 wherein the step of separating the plurality of sample fragments includes separating the plurality of sample fragments based upon a corresponding length of each of the plurality of sample fragments.

6. A method comprising the steps of:

providing a plurality of binding assays including a first binding assay and a second binding assay, the first binding assay for detecting any of $4^m$ different base sequences having a length of m bases, the second binding assay for detecting any of $4^n$ different base sequences having a length of n bases;

generating a first field within a first channel to separate, within the first channel, a plurality of unseparated sample fragments into a plurality of subsamples including a first subsample and a second subsample;

generating a second field in a second channel in communication with the first channel to isolate the first subsample within the second channel, wherein the second field is generally perpendicular to the first field;

generating a third field in a third channel in communication with the first channel to isolate the second subsample within the third channel, wherein the third field is generally perpendicular to the first field;

applying the first subsample isolated in the second channel to the first binding assay; and applying the second subsample isolated in the third channel to the second binding assay.

7. A method comprising the steps of:

providing a plurality of binding assays including a first binding assay and a second binding assay, the first binding assay for detecting any of $4^m$ different base sequences having a length of m bases, the second binding assay for detecting any of $4^n$ different base sequences having a length of n bases;

separating, within a first channel, a plurality of unseparated sample fragments into a plurality of subsamples including a first subsample and a second subsample;

isolating the first subsample within a second channel in communication with the first channel, wherein the second channel is generally perpendicular to the first channel;

isolating the second subsample within a third channel in communication with the first channel, wherein the third channel is generally perpendicular to the first channel;

applying the first subsample isolated in the second channel to the first binding assay; and applying the second subsample isolated in the third channel to the second binding assay.

8. A method comprising the steps of:

providing a plurality of binding assays including a first binding assay and a second binding assay;

separating, within a first channel, a plurality of unseparated sample fragments into a plurality of subsamples including a first subsample and a second subsample;

isolating the first subsample within a second channel connected to the first channel, the second channel having an outlet;

isolating the second subsample within a third channel connected to the first channel, the third channel having an outlet;

migrating the first subsample to the outlet of the second channel;

migrating the second subsample to the outlet of the third channel;

providing an applicator having a plurality of transfer elements including a first transfer element and a second transfer element;

loading the first subsample from the outlet of the second channel to the first transfer element;

loading the second subsample from the outlet of the third channel to the second transfer element; and contacting the applicator to a member which supports the plurality of binding assays to apply the first subsample to the first binding assay and the second subsample to the second binding assay.

9. The method of claim 8 further comprising the step of processing a sample of at least one polynucleotide to form the plurality of sample fragments.

10. The method of claim 9 wherein the sample is selected from the group consisting of a DNA sample and an RNA sample.

11. The method of claim 9 wherein the step of processing includes cutting the at least one polynucleotide in the sample using a restriction endonuclease.

12. The method of claim 6 wherein the plurality of sample fragments are separated based upon a corresponding length of each of the plurality of sample fragments.

13. The method of claim 6 wherein the plurality of sample fragments are separated based upon a corresponding mass of each of the plurality of sample fragments.

14. The method of claim 6 further comprising the step of processing a sample of at least one polynucleotide to form the plurality of sample fragments, the step of processing including cutting the at least one polynucleotide.

15. The method of claim 7 wherein the plurality of sample fragments are separated based upon a corresponding length of each of the plurality of sample fragments.

16. The method of claim 7 wherein the plurality of sample fragments are separated based upon a corresponding mass of each of the plurality of sample fragments.

17. The method of claim 7 further comprising the step of processing a sample of at least one polynucleotide to form the plurality of sample fragments, the step of processing including cutting the at least one polynucleotide.

18. The method of claim 8 wherein the plurality of sample fragments are separated based upon a corresponding length of each of the plurality of sample fragments.

19. The method of claim 8 wherein the plurality of sample fragments are separated based upon a corresponding mass of each of the plurality of sample fragments.

20. The method of claim 8 further comprising the step of processing a sample of at least one polynucleotide to form the plurality of sample fragments, the step of processing including cutting the at least one polynucleotide.

21. A method comprising the steps of:

separating a plurality of sample fragments into a plurality of subsamples including a first subsample and a second subsample;

applying the first subsample to a first binding assay for detecting any of $4^m$ different base sequences having a length of m bases; and applying the second subsample to a second binding assay for detecting any of $4^n$ different base sequences having a length of n bases;

wherein n is greater than m.

22. A method comprising the steps of:

separating a plurality of sample fragments into a plurality of subsamples including a first subsample and a second subsample, the second subsample having sample fragments of generally greater length than the first subsample;

applying the first subsample to a first binding assay for detecting any of $4^m$ different base sequences having a length of m bases; and applying the second subsample to a second binding assay for detecting any of $4^n$ different base sequences having a length of n bases;

wherein n is greater than m.

* * * * *